United States Patent
Grucela et al.

(10) Patent No.: US 10,029,043 B2
(45) Date of Patent: *Jul. 24, 2018

(54) PACKAGING SYSTEM FOR ANALYTE SENSORS

(71) Applicant: DexCom, Inc., San Diego, CA (US)

(72) Inventors: Minda McDorman Grucela, San Diego, CA (US); Jinsong Gao, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/625,840

(22) Filed: Jun. 16, 2017

(65) Prior Publication Data

US 2017/0290536 A1 Oct. 12, 2017

Related U.S. Application Data

(63) Continuation of application No. 14/617,197, filed on Feb. 9, 2015, now Pat. No. 9,717,843.
(Continued)

(51) Int. Cl.
| | |
|---|---|
| *A61M 5/00* | (2006.01) |
| *A61B 5/145* | (2006.01) |
| *A61B 50/33* | (2016.01) |
| *A61L 2/20* | (2006.01) |
| *A61B 50/20* | (2016.01) |

(Continued)

(52) U.S. Cl.
CPC ......... *A61M 5/003* (2013.01); *A61B 5/14532* (2013.01); *A61B 5/150022* (2013.01); *A61B 5/15087* (2013.01); *A61B 5/150305* (2013.01); *A61B 50/20* (2016.02); *A61B 50/30* (2016.02); *A61B 50/33* (2016.02); *A61L 2/08* (2013.01); *A61L 2/087* (2013.01); *A61L 2/20* (2013.01); *A61L 2/26* (2013.01); *A61B 2050/0057* (2016.02); *A61B 2050/0065* (2016.02); *A61B 2050/3008* (2016.02); *A61B 2560/04* (2013.01); *A61L 2202/24* (2013.01); *A61M 5/3287* (2013.01); *A61M 2205/33* (2013.01); *A61M 2205/3553* (2013.01); *A61M 2205/3561* (2013.01); *A61M 2205/3576* (2013.01); *A61M 2205/50* (2013.01)

(58) Field of Classification Search
CPC ............ A61B 5/14532; A61B 5/14536; A61B 5/150305; A61B 2050/0057; A61B 2050/0065; A61B 2560/04; A61L 2/08; A61L 2/087; A61L 2/20; A61L 2/26; A61L 2202/24; A61M 5/003; G01D 11/24; G01N 33/48; G01N 33/487; G01N 33/48778
USPC ....... 206/305, 363, 438, 569, 588–590, 592; 73/431; 422/401; 600/309, 345, 347, 600/365; 702/19
See application file for complete search history.

(56) References Cited

U.S. PATENT DOCUMENTS

| | | | |
|---|---|---|---|
| 3,759,375 A * | 9/1973 | Nappi | A45D 40/0087 206/370 |
| 4,511,035 A * | 4/1985 | Alpern | A61B 17/0682 206/363 |

(Continued)

*Primary Examiner* — Bryon Gehman
(74) *Attorney, Agent, or Firm* — Knobbe Martens Olson & Bear, LLP

(57) ABSTRACT

A system and method are provided for packaging and sterilizing analyte sensors. The packaging system provides a structure for securing the analyte sensors in a fixed position and fixed orientation within the package.

20 Claims, 14 Drawing Sheets

Related U.S. Application Data

(60) Provisional application No. 61/938,614, filed on Feb. 11, 2014.

(51) Int. Cl.
  *A61L 2/26* (2006.01)
  *A61B 5/15* (2006.01)
  *A61L 2/08* (2006.01)
  A61B 50/30 (2016.01)
  A61B 50/00 (2016.01)
  A61M 5/32 (2006.01)

(56) References Cited

U.S. PATENT DOCUMENTS

| | | | | |
|---|---|---|---|---|
| 5,575,403 A * | 11/1996 | Charlton | ............... | B01L 99/00 206/828 |
| 5,868,253 A * | 2/1999 | Krueger | ............... | A61F 2/0095 206/363 |
| 7,494,465 B2 * | 2/2009 | Brister | ............... | A61B 5/14532 600/300 |
| 8,252,229 B2 * | 8/2012 | Thomas | ............. | A61B 5/14532 600/347 |
| 8,275,437 B2 * | 9/2012 | Brauker | ............. | A61B 5/0031 600/345 |
| 8,396,528 B2 * | 3/2013 | Kamath | ............. | A61B 5/14865 600/345 |
| 8,478,377 B2 * | 7/2013 | Shariati | ................ | A61B 5/0031 600/345 |
| 8,684,172 B2 * | 4/2014 | Yao | ..................... | B65D 43/162 206/204 |
| 8,802,006 B2 * | 8/2014 | Thomas | ............. | A61B 5/14532 600/347 |
| 9,101,305 B2 * | 8/2015 | Larson | ............... | A61B 5/14532 |
| 9,239,252 B2 * | 1/2016 | Koga | ............... | G01N 33/48771 |
| 2012/0227358 A1 | 9/2012 | Larson et al. | | |

\* cited by examiner

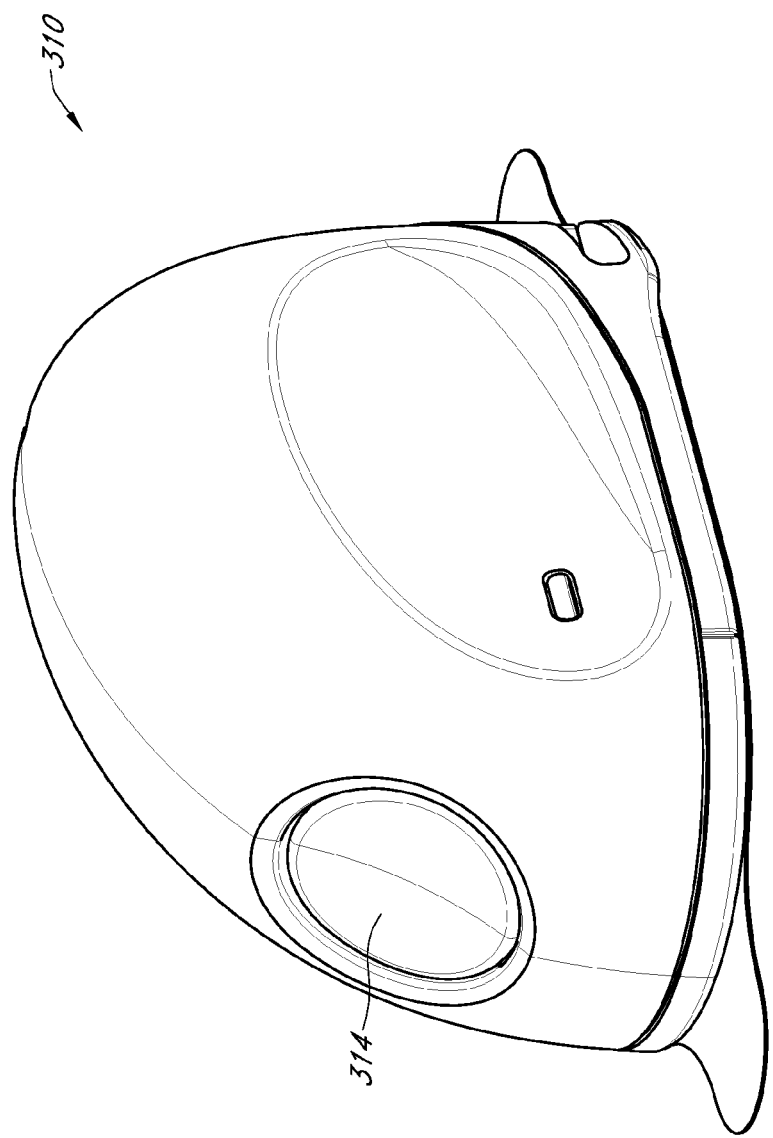

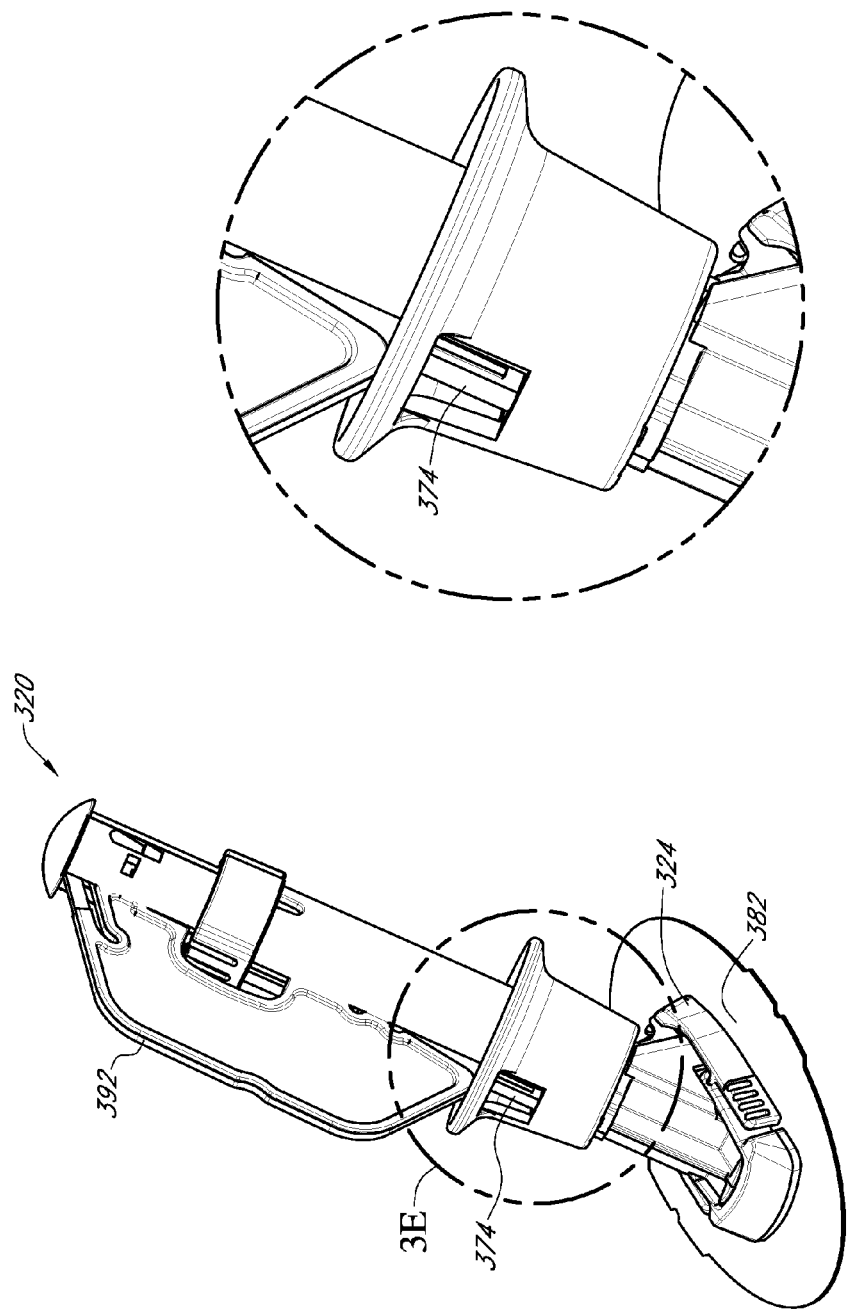

PACKAGING SYSTEM FOR ANALYTE SENSORS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 14/617,197, filed on Feb. 9, 2015, which claims the benefit of U.S. Provisional Application No. 61/938,614, filed on Feb. 11, 2014. Each of the aforementioned applications is incorporated by reference herein in its entirety, and each is hereby expressly made a part of this specification.

TECHNICAL FIELD

The embodiments disclosed herein relate to a system and method for packaging analyte sensors. In particular embodiments, the analyte sensors are glucose sensors for use with implantable continuous glucose monitor systems.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter that transmits measurement data to a receiver that processes and displays information based on the measurements. Such sensor systems are sometimes referred to as continuous glucose monitors (CGMs).

Continuous glucose sensors are typically transported by the use of various sterile package systems. One common method for packaging implantable sensors involves "bagging" the device in a flexible bag. Because the glucose sensors are not secured in fixed positions, these sensors will often shift and tumble within the package when the package is moved. Because of susceptibility to movement of sensors within the package and because of uneven distribution of radiation emitted to different positions within the package, sterilization of glucose sensors typically requires that the package is subjected to a substantially higher dosage of radiation than what would be required if the glucose sensors were secured to fixed positions within the package. Accordingly, in many instances, the dosage emitted is at a setting such that the different locations of within the package may receive a radiation dosage from about 25 kGray to about 35 kGray.

Not only is this a wide range of radiation dosage, but the high overall dosage is required to ensure that the sterilization meets the required standards to account for the possibility that the glucose sensors may shift to locations within the package that receive a lower dosage of radiation than other locations that receive a higher dosage of radiation. Consequently, for various reasons, a glucose sensor that receives a higher dosage of radiation (e.g., 35 kGray) may have a shortened sensor lifetime, as compared to a glucose sensor that receives a lower dosage of radiation (e.g., 25 kGray). For example, a higher dosage of radiation can denature a percentage of the glucose sensor's enzymes used to break down glucose to produce a measured species indicative of glucose concentration. Additionally, a higher overall dosage of radiation may also damage the adhesiveness of the adhesive patch used to adhere an ex vivo portion of a glucose sensor system to the skin. Furthermore, another drawback to the use of a higher overall dosage of radiation is that potential damage to the package—for example, damage to ink printed on the package/container to provide graphics and damage to certain contents (e.g., an instruction manual) received by the package—becomes more pervasive at high radiation dosages. Heretofore, a separate package/container was used to hold the glucose sensor during the sterilization process. Afterwards, the glucose sensor was taken out of the sterilization package and then placed into a final package which is then shipped out for use.

Conventionally, the radiation dosage range often used is from about 25 kGray to about 35 kGray for implantable glucose sensors. With the product advantage of having the products secured in a fixed position and fixed orientation, such that each product receives substantially an equal dosage of the radiation, the higher end of the setting range can be lowered to reduce the risk of enzyme denaturing. For example, in one embodiment, the radiation dosage range applied may be from about 25 kGray to about 30 kGray. In still another embodiment, lower radiation setting of the range may be about 10 kGray, 15 kGray, 20 kGray, or 25 kGray, and the upper radiation setting of the range may be about 25 kGray, 30 kGray, or 35 kGray.

When a package contains a plurality of glucose sensors, and these sensors are shifted to different positions and/or orientations within a package prior to or during sterilization, the sensors may each receive different amounts of radiation and a different radiation profile. This difference in radiation dosage may result in inconsistent sensor properties and thus inconsistent sensor performance among sensors. Accordingly, it is desirable to package the glucose sensors in a manner that prevents or substantially minimizes sensor movement within the package. It is also desirable to sterilize the glucose sensors in a manner that permits substantial consistency in radiation dosage received and substantial consistency in radiation profile.

SUMMARY

The present embodiments have several features, no single one of which is solely responsible for their desirable attributes. Without limiting the scope of the present embodiments as expressed by the claims that follow, their more prominent features will now be discussed briefly. After considering this discussion, and particularly after reading the section entitled "Detailed Description," one will understand how the features of the present embodiments provide the advantages described herein.

In a first aspect, a package is provided for receiving and securing a product, the package comprising: a product comprising an implantable continuous glucose sensor; at least one first container configured to receive and secure the product therein; a second container configured to receive the at least one first container; and a retainer configured to secure the at least one first container in a fixed position and fixed orientation within the second container such that movement of the second container does not result in movement of the first container within the second container.

In an embodiment of the first aspect, the at least one first container comprises a plurality of first containers, wherein the at least one region of the retainer comprises a plurality of regions each configured to secure one of the plurality of first containers.

In an embodiment of the first aspect, the plurality of regions of the retainer are spaced apart at an equal distance such that the plurality of first containers are spaced apart at an equal distance.

In an embodiment of the first aspect, the plurality of products are aligned in a uniform orientation.

In an embodiment of the first aspect, the retainer is an integral component of the second container.

In an embodiment of the first aspect, the retainer is an insert releasably attached to the second container.

In an embodiment of the first aspect, the region of the retainer comprises an aperture or pocket shaped to receive and conform to a region of the first container.

In an embodiment of the first aspect, the product further comprises a housing configured to receive an electronics unit, wherein the housing comprises an adhesive configured to attach the housing to the host.

In an embodiment of the first aspect, the product further comprises an insertion device configured to insert the implantable continuous glucose sensor into the host.

In an embodiment of the first aspect, the first container comprises a shaped layer and a backing layer adhered to the shaped layer.

In an embodiment of the first aspect, the backing layer comprises a material selected from the group consisting of: polyvinyl chloride, polyvinylidenechloride, polyacrylonitrile, polyethylene, polyethylene terephthalate, polyethylene naphthalate, polypropylene, polyacrylate, cyclic olefins, polystyrene, polyesters, polyamides, ethylene vinyl alcohol, polyvinyl alcohol, and copolymers thereof; and paper.

In an embodiment the first aspect, the shaped layer is a molded part with a chamber for receiving the product.

In an embodiment of the first aspect, the shaped layer is formed of a film.

In an embodiment of the first aspect, the film comprises a polymer selected from the group consisting of: polyvinyl chloride, polyethylene, polyethylene terephthalate, polyethylene terephthalate glycol, polyvinylidene chloride, polypropylene, polyethylene, styrene, and copolymers thereof.

In an embodiment of the first aspect, the shaped layer comprises at least one region configured to secure the product in a fixed position and fixed orientation within the at least one first container such that movement of the at least one first container and/or the second container does not result in movement of the product within the at least one first container.

In an embodiment of the first aspect, the at least one region of the shaped layer comprises a plurality of regions configured to secure the product in a fixed position and fixed orientation within the at least one first container.

In an embodiment of the first aspect, the shaped layer is shaped and dimensioned to prevent bending of the adhesive patch.

In an embodiment of the first aspect, the product further comprises a third container, wherein the third container is dimensioned and configured to receive a plurality of second containers and secure the plurality of second containers in a fixed position and fixed orientation.

In an embodiment of the first aspect, the third container is dimensioned and configured to hold only one level of a plurality of second containers.

Any of the aforementioned embodiments of the first aspect can be combined with one or more other embodiments of the first aspect.

In a second aspect, a method is provided for sterilizing a product, the method comprising: securing a product in a fixed position and fixed orientation within a first container such that movement of the first container does not result in movement or orientation change of the product within the first container, wherein the product comprises an implantable continuous glucose sensor; repeating securing a product in a first container; securing a plurality of first containers in a fixed position and fixed orientation within the second container such that a plurality of products are in a uniform orientation and such that movement of the second container does not result in movement or orientation change of the plurality of products within the second container; moving the second container to a sterilization apparatus; and sterilizing the plurality of products such that each of the plurality of products receive an equal dose of radiation.

In an embodiment of the second aspect, moving the second container is performed by a conveyor system.

In an embodiment of the second aspect, sterilizing is performed by light-based sterilization.

In an embodiment of the second aspect, securing a product is performed by securing the product in a shaped layer and attaching a backing layer to the shaped layer to create a seal.

In an embodiment of the second aspect, the shaped layer is a molded part with a chamber for receiving the product.

In an embodiment of the second aspect, the shaped layer is formed of a film.

In an embodiment of the second aspect, the film comprises a polymer selected from the group consisting of: polyvinyl chloride, polyethylene, polyethylene terephthalate, polyethylene terephthalate glycol, polyvinylidene chloride, polypropylene, polyethylene, styrene, and copolymers thereof.

In an embodiment of the second aspect, the shaped layer comprises at least one region configured to secure the product in a fixed position and fixed orientation within the at least one first container such that movement of the first container and/or the second container does not result in movement of the product within the first container.

In an embodiment of the second aspect, the product comprises an implantable continuous glucose sensor and a housing configured to receive an electronics unit, wherein the housing comprises an adhesive patch configured to attach the housing to the host.

In an embodiment of the second aspect, the shaped layer is shaped and dimensioned to prevent bending of the adhesive patch.

In an embodiment of the second aspect, securing a plurality of first containers in a fixed position and fixed orientation within the second container is performed by aligning and affixing a region of the first container to a retainer.

In an embodiment of the second aspect, the retainer comprises an aperture or pocket shaped to receive and conform to the region of the first container.

In an embodiment of the second aspect, the method further comprises securing a plurality of second containers in a fixed position and fixed orientation within a third container such that a plurality of products are in a uniform orientation and such that movement of the third container does not result in movement or orientation change of the plurality of products within the second container and the first container.

In an embodiment of the second aspect, the method further comprises moving the third container to a sterilization apparatus; and sterilizing the plurality of products such that each of the plurality of products receive an equal dose of radiation.

In an embodiment of the second aspect, the third container is dimensioned and configured to hold only one level of a plurality of second containers.

Any of the aforementioned embodiments of the second aspect can be combined with one or more other embodiments of the second aspect.

In a third aspect, a kit is provided comprising: a product comprising an implantable glucose sensor; at least one first container configured to receive and secure the product therein; a second container configured to receive the at least one first container; and a retainer comprising at least one a region configured to secure the at least one first container in a fixed position and fixed orientation within the second container such that movement of the second container does not result in movement of the first container within the second container.

In an embodiment of the third aspect, the product further comprises a housing configured to receive an electronics unit, wherein the housing comprises an adhesive configured to attach the housing to the host.

In an embodiment of the third aspect, the product further comprises an insertion device configured to insert the implantable glucose sensor into a host.

Any of the aforementioned embodiments of the third aspect can be combined with one or more other embodiments of the third aspect.

The method of the second aspect and the various embodiments thereof can be combined with the package of the first aspect and the various embodiments thereof and/or the kit of the third aspect and the various embodiments thereof. Similarly, the package of the first aspect can be combined with the kit of the third aspect.

BRIEF DESCRIPTION OF THE DRAWINGS

The present embodiments have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

FIG. 3A is a perspective view of one embodiment a sensor insertion device.

FIG. 3D is another perspective view of the embodiment illustrated in FIG. 3B.

FIG. 3E is a close-up view of a portion of the embodiment illustrated in FIG. 3D.

DETAILED DESCRIPTION

Figure 1:
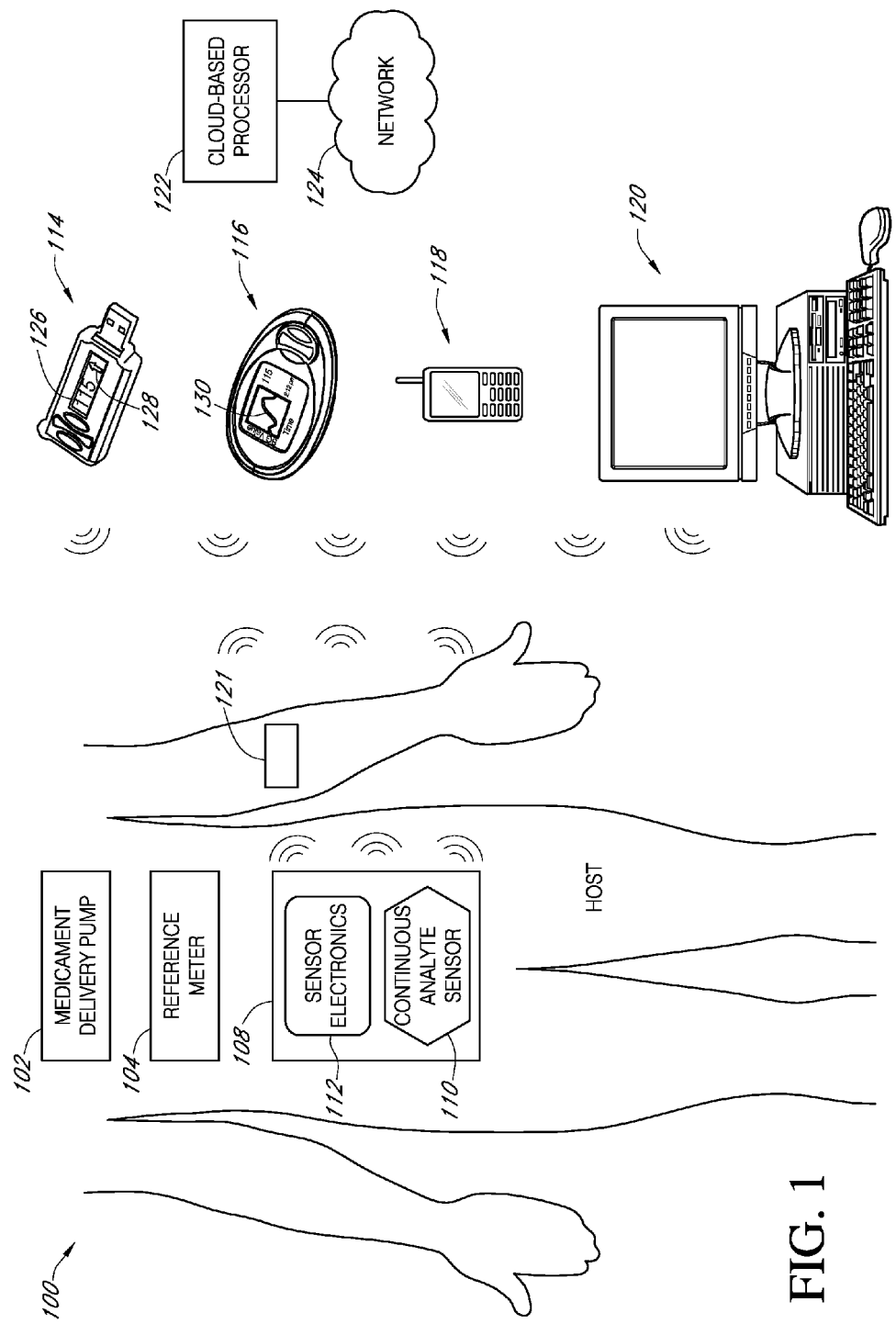
FIG. 1 is a schematic view of one embodiment of a continuous analyte sensor system attached to a host and communicating with other devices.

The following detailed description describes the present embodiments with reference to the drawings. In the drawings, reference numbers label elements of the present embodiments. These reference numbers are reproduced below in connection with the discussion of the corresponding drawing features. Dimensions of certain parts shown in the drawings may have been modified and/or exaggerated for the purposes of clarity or illustration.

The present embodiments are described below with reference to the figures. These figures, and their written descriptions, may indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unitary piece.

Continuous Analyte Monitoring System

For illustrative purposes, reference will now be made to FIG. 1, which is an example environment in which some embodiments described herein may be implemented. Here, an analyte monitoring system 100 includes a continuous analyte sensor system 108. Continuous analyte sensor system 108 includes a sensor electronics module 112 and a continuous analyte sensor 110. The system 100 can also include other devices and/or sensors, such as a medicament delivery pump 102 and a reference analyte meter 104, as illustrated in FIG. 1. The continuous analyte sensor 110 may be physically connected to sensor electronics module 112 and may be integral with (e.g., non-releasably attached to) or releasably attachable to the continuous analyte sensor 10. Alternatively, the continuous analyte sensor 110 may be physically separate to sensor electronics module 112, but electronically coupled via inductive coupling or the like. Further, the sensor electronics module 112, medicament delivery pump 102, and/or analyte reference meter 104 may communicate with one or more additional devices, such as any or all of display devices 114, 116, 118, 120, and 121.

The system 100 of FIG. 1 also includes a cloud-based processor 122 configured to analyze analyte data, medicament delivery data, and/or other patient related data provided over network 124 directly or indirectly from one or more of sensor system 108, medicament delivery pump 102, reference analyte meter 104, and display devices 114-121. Based on the received data, the processor 122 can further process the data, generate reports providing statistic based on the processed data, trigger notifications to electronic devices associated with the host or caretaker of the host, or provide processed information to any of the other devices of FIG. 1. In some example implementations, the cloud-based processor 122 comprises one or more servers. If the cloud-based processor 122 comprises multiple servers, the servers can be either geographically local or separate from one another. The network 124 can include any wired and wireless communication medium to transmit data, including WiFi networks, cellular networks, the Internet and any combinations thereof.

It should be understood that although the example implementation described with respect to FIG. 1 refers to analyte data being received by processor 122, other types of data processed and raw data may be received as well.

In some example implementations, the sensor electronics module 112 may include electronic circuitry associated with measuring and processing data generated by the continuous analyte sensor 110. This generated continuous analyte sensor data may also include algorithms, which can be used to process and calibrate the continuous analyte sensor data, although these algorithms may be provided in other ways as well. The sensor electronics module 112 may include hardware, firmware, software, or a combination thereof to provide measurement of levels of the analyte via a continuous analyte sensor, such as a continuous glucose sensor.

The sensor electronics module 112 may, as noted, couple (e.g., wirelessly and the like) with one or more devices, such as any or all of display devices 114, 116, 118, 120, and 121. The display devices 114, 116, 118, 120, and/or 121 may be configured for processing and presenting information, such sensor information transmitted by the sensor electronics module 112 for display at the display device. The display devices 14, 16, 18, 20, and 21 can also trigger alarms based on the analyte sensor data.

In FIG. 1, display device 114 is a key fob-like display device, display device 16 is a hand-held application-specific computing device 116 (e.g., the Dexcom G4® Platinum receiver commercially available from Dexcom, Inc.), display device 18 is a general purpose smart phone or tablet computing device 120 (e.g., an Apple® iPhone®, iPad®, or iPod Touch® commercially available from Apple, Inc.), display device 120 is a computer workstation 120, and display device 121 is any wearable. In some example implementations, the relatively small, key fob-like display device 114 may be a computing device embodied in a wrist watch, a belt, a necklace, a pendent, a piece of jewelry, an adhesive patch, a pager, a key fob, a plastic card (e.g., credit card), an identification (ID) card, and/or the like. This small display device 114 may include a relatively small display (e.g., smaller than the display device 118) and may be configured to display a limited set of displayable sensor information, such as a numerical value 126 and/or an arrow 128. In contrast, display devices 116, 118, and 120 can be larger display devices that can be capable of displaying a larger set of displayable information, such as a trend graph 130 depicted on the hand-held receiver 116 in addition to other information such as a numerical value and arrow.

It is understood that any other user equipment (e.g., computing devices) configured to at least present information (e.g., a medicament delivery information, discrete self-monitoring analyte readings, heart rate monitor, caloric intake monitor, and the like) can be used in addition or instead of those discussed with reference to FIG. 1.

In some example implementations of FIG. 1, the continuous analyte sensor 110 comprises a sensor for detecting and/or measuring analytes, and the continuous analyte sensor 110 may be configured to continuously detect and/or measure analytes as a non-invasive device, a subcutaneous device, a transdermal device, and/or an intravascular device. In some example implementations, the continuous analyte sensor 110 may analyze a plurality of intermittent blood samples, although other analytes may be used as well.

In some example implementations of FIG. 1, the continuous analyte sensor 110 may comprise a glucose sensor configured to measure glucose in the blood using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 110 includes a glucose sensor, the glucose sensor may comprise any device capable of measuring the concentration of glucose and may use a variety of techniques to measure glucose including invasive, minimally invasive, and non-invasive sensing techniques (e.g., fluorescent monitoring), to provide a data, such as a data stream, indicative of the concentration of glucose in a host. The data stream may be raw data signal, which is converted into a calibrated and/or filtered data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 110 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

In some implementations of FIG. 1, the continuous analyte sensor system 8 includes a Dexcom G4® Platinum glucose sensor and transmitter commercially available from Dexcom, Inc., for continuously monitoring a host's glucose levels.

Sensor System

The preferred embodiments relate to the use of an analyte sensor that measures a concentration of glucose or a substance indicative of the concentration or presence of the analyte. In some embodiments, the analyte sensor is a continuous device, for example a subcutaneous, transdermal, transcutaneous, and/or intravascular (e.g., intravenous) device. In some embodiments, the device can analyze a plurality of intermittent blood samples. The analyte sensor can use any method of glucose-measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The analyte sensor can use any known method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

Although much of the description and examples are drawn to a glucose sensor, the systems and methods of the preferred embodiments can be applied to any measurable analyte. In some preferred embodiments, the analyte sensor is a glucose sensor capable of measuring the concentration of glucose in a host. One example embodiment is described below, which utilizes an implantable glucose sensor. However, it should be understood that the devices and methods described herein can be applied to any device capable of detecting a concentration of analyte and providing an output signal that represents the concentration of the analyte.

In one preferred embodiment, the analyte sensor is a wholly implantable glucose sensor, such as described with reference to U.S. Pat. No. 6,001,067 and U.S. Patent Publication No. US-2011-0027127-A1. In another preferred embodiment, the analyte sensor is a transcutaneous glucose sensor, such as described with reference to U.S. Patent Publication No. US-2006-0020187-A1. In yet another preferred embodiment, the analyte sensor is a dual electrode analyte sensor, such as described with reference to U.S. Patent Publication No. US-2009-0137887-A1. In still other embodiments, the sensor is configured to be implanted in a host vessel or extracorporeally, such as is described in U.S. Patent Publication No. US-2007-0027385-A1.

The term "analyte" as used herein is a broad term, and is to be given its ordinary and customary meaning to a person of ordinary skill in the art (and it is not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to lactate or lactic acid; cardiac markers; ketone bodies; acetone; acetoacetic acid; beta hydroxybutyric acid; glucagon, acetyl Co A; intermediaries in the Citric Acid Cycle; choline, testosterone; creatinine; triglycerides; sodium; potassium; chloride; bicarbonate; total protein; alkaline phosphatase; calcium; phosphorus; $PO_2$; $PCO_2$; bilirubin (direct and total); red blood cell count; white blood cell count; hemoglobin; hemactocrit; lymphocytes; monocytes; eosinophils; basophils; c-reactive protein; cryoglobulins; fibrinogens; ACTH; aldosterone; ammonia; beta-HCG; magnesium; copper; iron; total cholesterol; low density lipoproteins; high density lipoproteins; lipoprotein A; T4 (total and free); TSH; FSH; LH; ACTH; hepatitis BE antigen; hepatitis B surface antigen; hepatitis A antibody; hepatitis C antibody; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies A, S, C, and E, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

Figure 2:
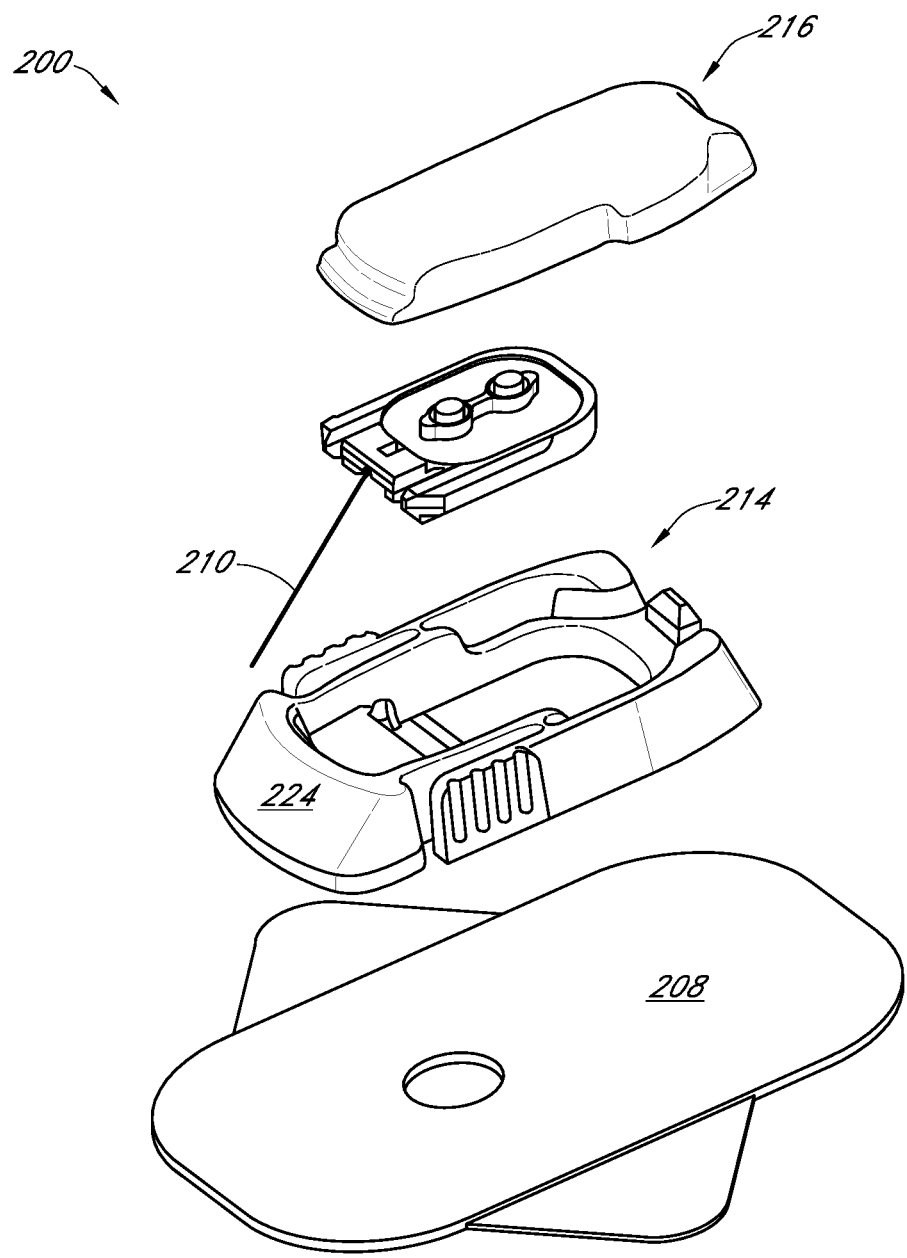
FIG. 2 is an exploded perspective view of one embodiment of a transcutaneous sensor system.

FIG. 2 illustrates an exploded perspective view of a transcutaneous sensor system 200. In this particular embodiment, the sensor 210 is operably attached to an on-skin electronics housing unit 214, also referred to as a housing 214, configured to receive electronics 216. The housing 214 comprises a base 224 adapted for fastening to a host's skin. The base 224 can be formed from a variety of hard or soft materials, and preferably comprises a low profile for minimizing protrusion of the device from the host during use. In some embodiments, the base 224 is formed at least partially from a flexible material, which is believed to provide numerous advantages over conventional transcutaneous sensors, which, unfortunately, can suffer from motion-related artifacts associated with the host's movement when the host is using the device. For example, when a transcutaneous analyte sensor 210 is inserted into the host, various movements of the sensor 210 (for example, relative movement between the in vivo portion and the ex vivo portion, movement of the skin, and/or movement within the host (dermis or subcutaneous)) create stresses on the device and can produce noise in the sensor signal. It is believed that even small movements of the skin can translate to discomfort and/or motion-related artifact, which can be reduced or obviated by a flexible or articulated base. Thus, by providing flexibility and/or articulation of the device against the host's skin, better conformity of the sensor system to the regular use and movements of the host can be achieved. Flexibility or articulation is believed to increase adhesion (with the use of an adhesive pad or patch) of the electronics housing unit onto the skin, thereby decreasing motion-related artifact that can otherwise translate from the host's movements and reduced sensor performance.

The process of applying the sensor to the person is important for such a system to be effective and user friendly. The application process should result in the sensor assembly being attached to the person in a state where it is capable of sensing glucose level information, communicating the glucose level information to the transmitter, and transmitting the glucose level information to the receiver.

Figure 3C:
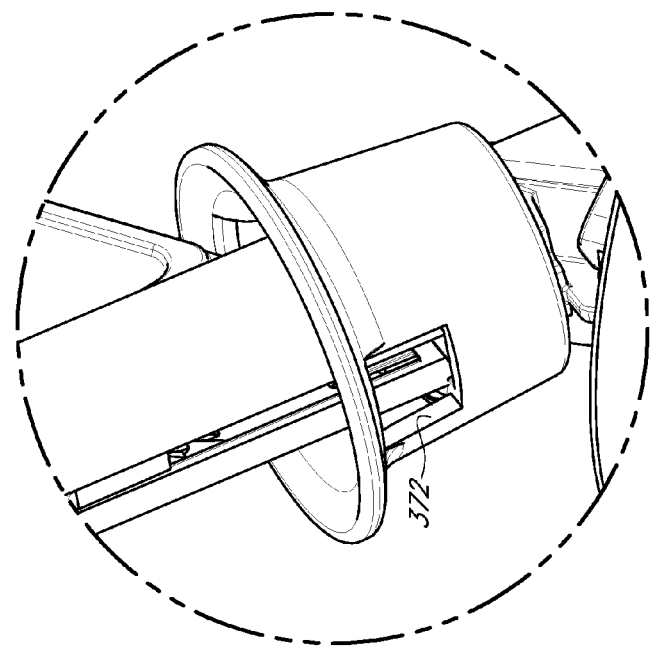
FIG. 3C is a close-up view of a portion of the embodiment illustrated in FIG. 3B.
Figure 3B:
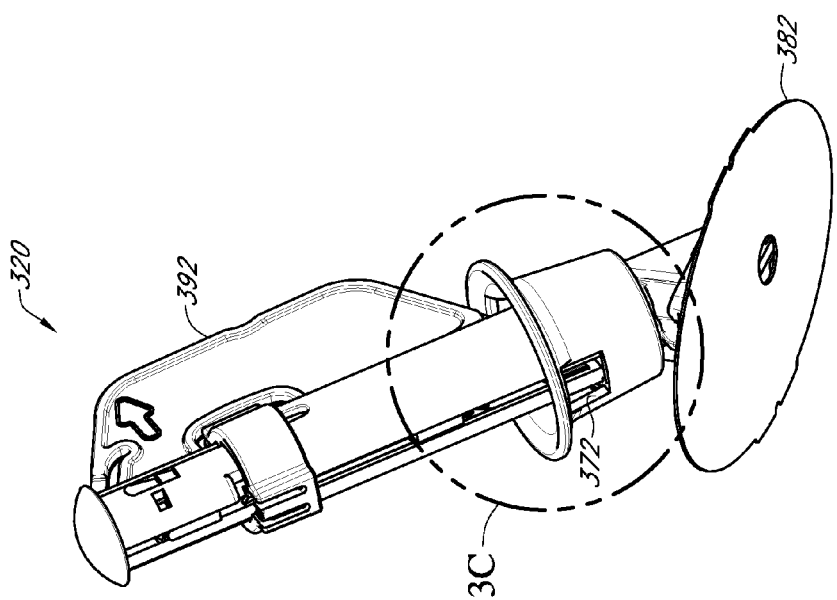
FIG. 3B is a perspective view of another embodiment of a sensor insertion device.

In some embodiments, such as the embodiments illustrated in FIGS. 3A and 3B, the sensor insertion device 310, 320 may employ an automatic, semi-automatic, or manual mechanism for implanting a sensor in a host. The expression "sensor insertion device" as used herein is a broad term, and is to be given its ordinary and customary meaning to a person of ordinary skill in the art (and it is not to be limited to a special or customized meaning), and refers without limitation to a device comprising a sensor insertion mechanism employed to insert a sensor into a host.

In one embodiment, as illustrated in FIG. 3A, the sensor insertion device 310 includes a base configured to secure a housing (not shown) configured to receive an electronics unit (not shown) configured to generate analyte information based on a signal from a sensor. The sensor insertion device 310 also includes a sensor insertion mechanism (not shown) configured to insert the sensor into the host and a trigger 314 configured (in response to activation) to cause the sensor insertion mechanism to insert the sensor into the host and to cause the housing to detach from the base. In one embodiment, the sensor mechanism is configured, in response to the activation of the trigger 314, to rotate a component (e.g., a wheel) in response to a torque from the torsion spring, whereby a needle is caused to be inserted into the host and to be retracted from the host thereafter.

In another embodiment, as illustrated in FIGS. 3B and 3D, the sensor insertion device 320 employs a substantially manual mechanism for sensor insertion. The sensor insertion device 320 includes an insertion device body that aides in aligning and guiding the insertion device components. Preferably, the insertion device body includes an insertion device body base that engages an on-skin housing 324 configured to receive an electronics unit. The sensor insertion mechanism comprises a guide tube subassembly that includes a guide tube carrier and a guide tube (both not shown). In some embodiments, the guide tube is a cannula. The guide tube carrier slides along the insertion device body and maintains the appropriate relative position of the guide tube during sensor insertion and subsequent retraction of the guide tube. The insertion device 320 also includes a plunger subassembly comprising a plunger and plunger cap. The plunger subassembly cooperates with other insertion device components to ensure proper insertion and subsequent retraction of the insertion device components. As illustrated in FIGS. 3B and 3D and as described in the Packaging System section, in some embodiments, the sensor insertion device may comprise one or more notches, 372, 374 that are configured to securely engage one or more portions of a protective package. Close-up views of these notches are illustrated in FIGS. 3C and 3E. The above-described engagement helps secure the sensor insertion device and any other components attached thereto to the protective package, such that movement of the protective package does not result in a shift in the position or orientation of the sensor insertion device relative to the protective package.

Packaging System

As described elsewhere herein, conventional techniques for packaging implantable glucose sensors typically involves placing one or more sensors in a flexible bag wherein the sensors are not secured in a fixed position and fixed orientation. Consequently, the sensors packaged using these techniques will often shift and tumble within the package during movement of the package. In preferred embodiments described herein, a packaging system is provided that provides a mechanism for securing the sensors in a manner that prevents sensor movement within the package.

The preferred embodiments relate to the use of a packaging system that receives a medical device product prior to, during, and after sterilization. The term "product" as used herein is a broad term, and is to be given its ordinary and customary meaning to a person of ordinary skill in the art (and it is not to be limited to a special or customized meaning), and refers without limitation to a medical device that is designed to be received by a container or package. In certain embodiments, the product being packaged may comprise any of a variety of sensor insertion devices and/or analyte sensors. For example, in one embodiment, the product may consist only of an implantable continuous glucose sensor. In another embodiment, the product may include an on-skin sensor assembly comprising an implantable continuous glucose sensor and a housing configured to receive an electronics unit operatively connected to the sensor. In still another embodiment, the product may include the above-described on-skin assembly (comprising the implantable continuous glucose and the housing) and any of a variety of sensor insertion devices configured to insert the sensor into the host.

Figure 4A:
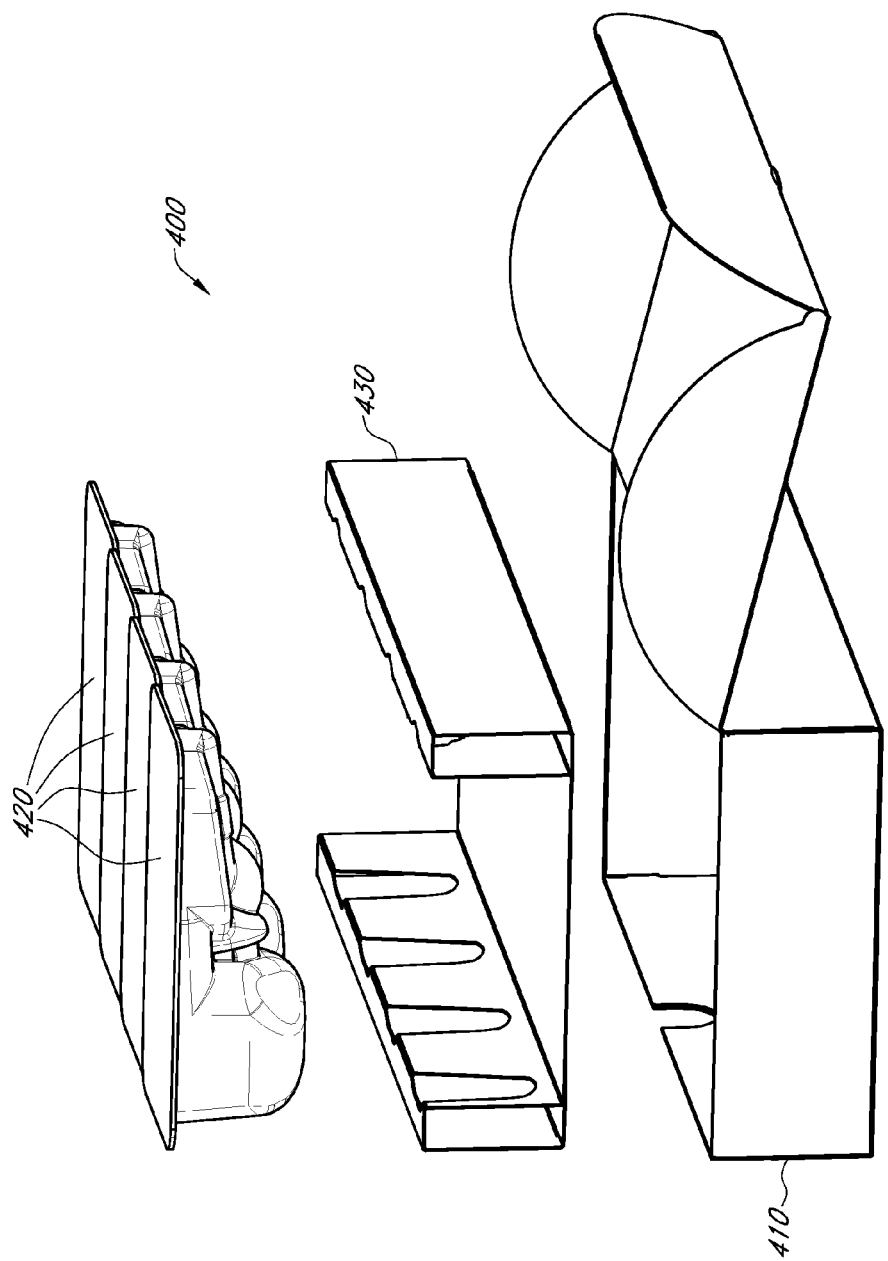
FIG. 4A is an exploded perspective view of one embodiment of a packaging system.
Figure 4B:
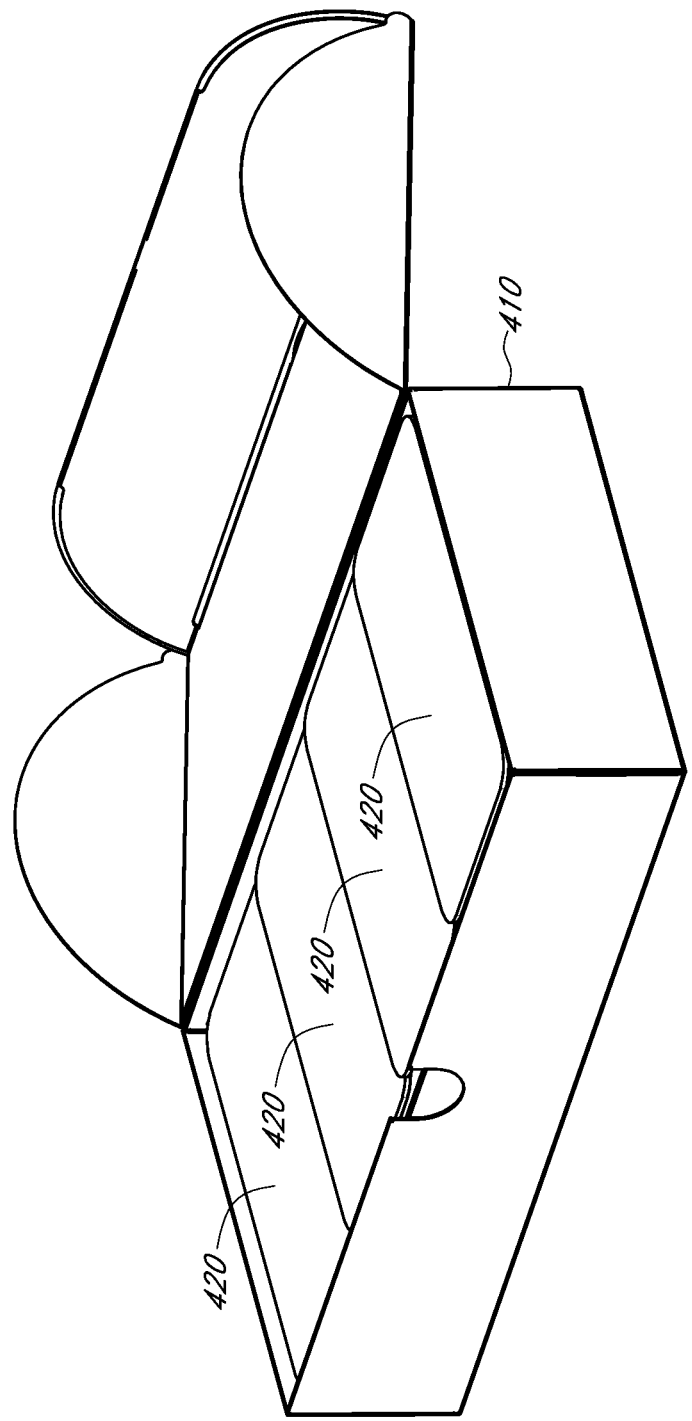
FIG. 4B is a perspective view of the embodiment shown in FIG. 4A, after the retainer and protective packages have been placed into the secondary container.
Figure 4C:
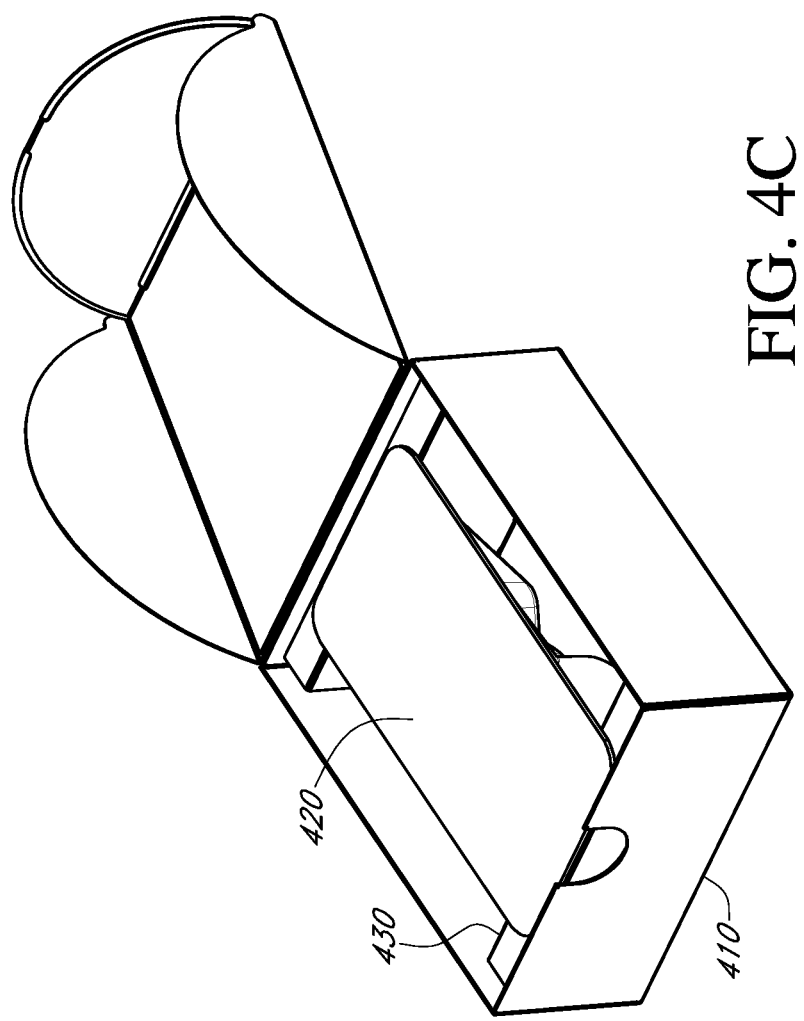
FIG. 4C is a perspective view of another embodiment of a packaging system, after the retainer and a protective package have been placed into the secondary container.
Figure 5A:
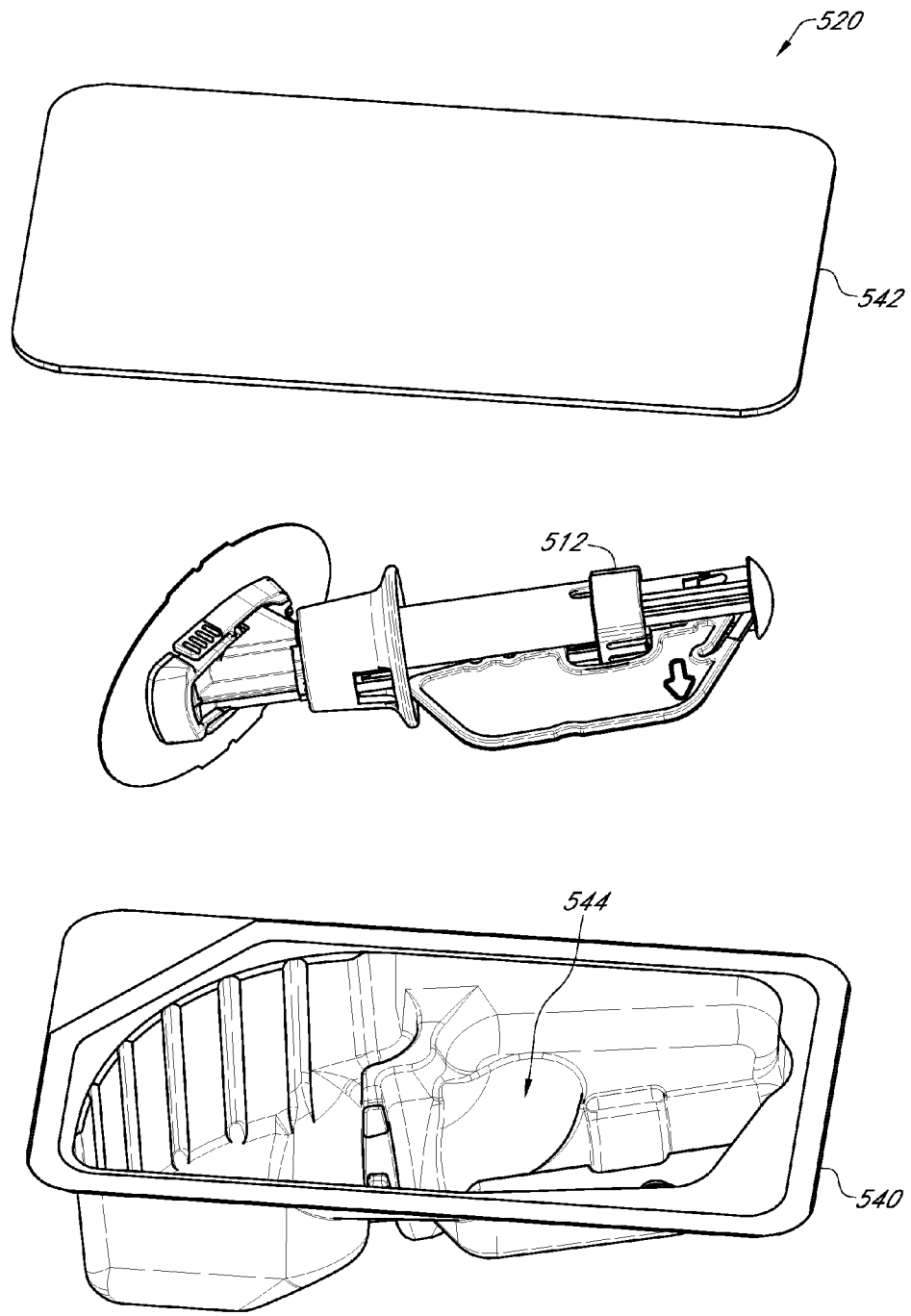
FIG. 5A is a an exploded view of a protective package configured to receive a product comprising an implantable continuous glucose sensor, an on-skin housing configured to receive an electronics unit operatively connected to the sensor, and a sensor insertion device.
Figure 5B:
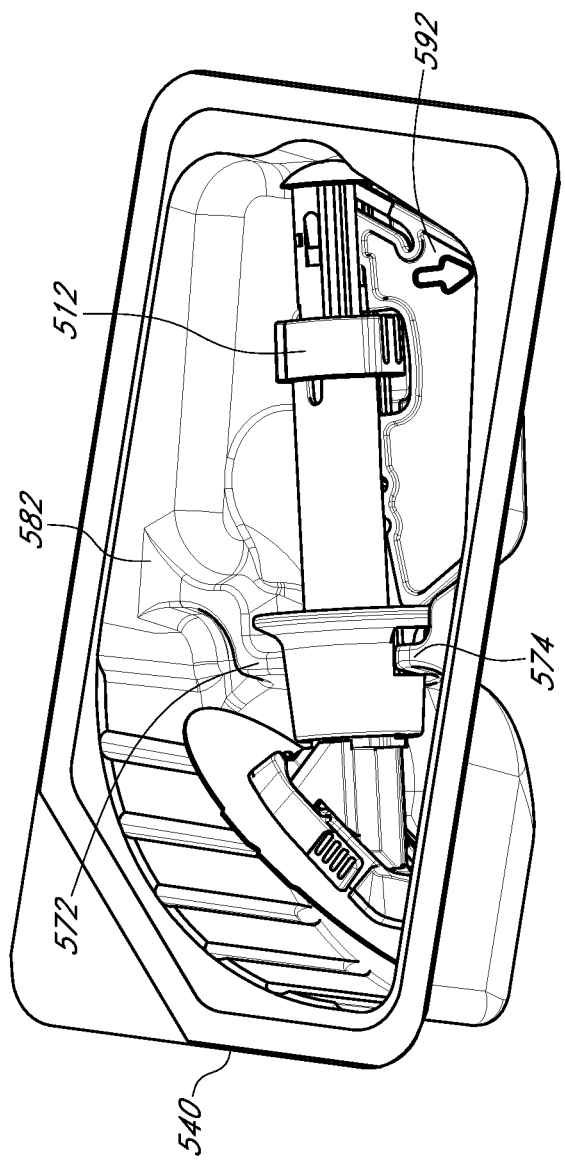
FIG. 5B is a perspective view of a medical device product placed into a shaped layer.
Figure 5C:
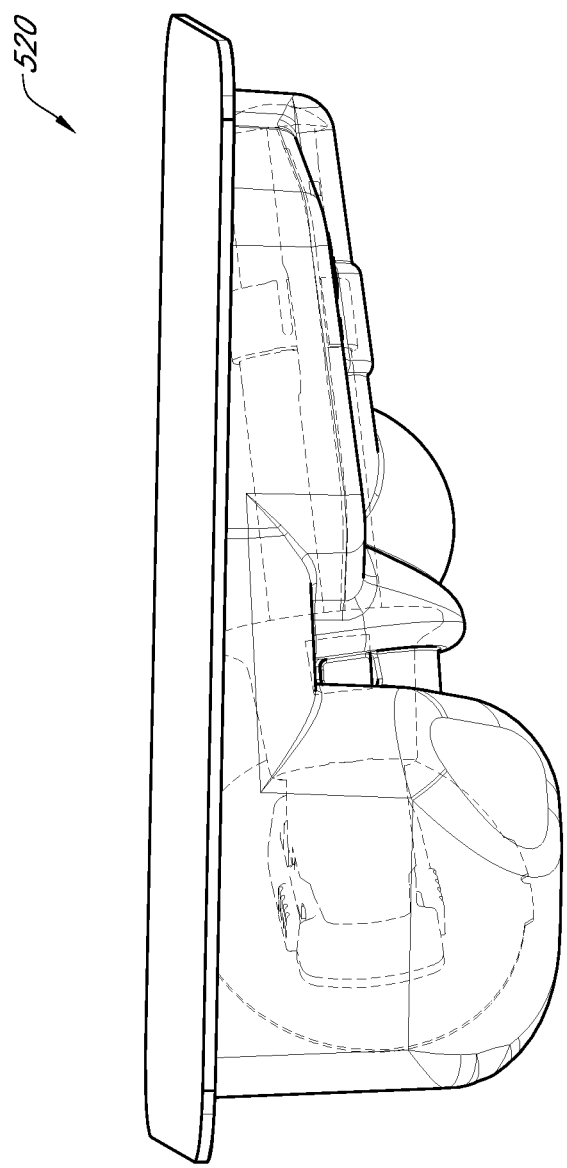
FIG. 5C is a perspective view of the protective package of FIG. 5A after it has been assembled and sealed.

FIG. 4A shows an exploded perspective view one embodiment of a package system 400 for packaging a plurality of medical device products. The package system 400 includes a secondary container 410 that receives at least one protective package or container 420. In turn, as illustrated in FIG. 5A-5C, each protective package 420, 520 receives at least one medical device product. The package system 400 may also include a retainer 430 designed to secure the protective package(s) 420 in a fixed position and fixed orientation within the secondary container 410, such that movement of the secondary container 410 will not likely result in movement of the protective package 420 within the secondary container 410. FIG. 4B illustrates a perspective view of the embodiment shown in FIG. 4A after the retainer 430 and protective packages 420 have been placed into the secondary container 410. In should be understood that although the in the embodiments described with reference to FIGS. 4A and 4B, the packaging system 400 is designed to hold and secure four products, in other embodiments, the packaging system 400 may be designed to hold any of a number of products, such as two, three, five, six, nine, ten, twelve, sixteen, twenty or more products. For example, as illustrated in FIG. 4C, in one embodiment, the packaging system 400 is designed to hold one protective package with a product therein.

Referring to FIG. 5A, which provides an exploded view, the protective package 520 may be formed of a shaped layer 540 sealed (or otherwise bonded) to a backing layer 542. The shaped layer 540 has a compartment 544 or other type of deformation formed therein such that upon sealing of the shaped layer 540 to the backing layer 542 a compartment is formed for holding or containing the medical device product 512. The product compartment 544 may be accessed by removing the backing layer 542 from the package 520 to expose the compartment 544 and the medical device product 512 held therein. In some embodiments, an edge portion of the backing layer is configured to not adhere to the shaped layer 540, so as to simplify tearing of the backing layer off the shaped layer. In other embodiments, a starting notch may be provided to facilitate tearing the edge of the protective package toward the compartment.

The shaped layer 540 and the backing layer 542 may be sealed together, such as by conduction or any sealing method known in the art, to prevent ready access to the medical device product 512 held therein. In some embodiments, a hermetic seal is formed. The shaped layer 540 may be formed from any of a variety of rupture-resistant, semi-rigid material. Any thermoformed material used in blister packaging, such as plastic, may be used. Materials that may be used to form the shaped layer include polyvinyl chloride, polyethylene, polyethylene terephthalate, polyethylene terephthalate glycol, polyvinylidene chloride, polypropylene, polyethylene, styrene, copolymers or combinations thereof, or other suitable materials for packaging. The material may be a single ply or multiple plies or laminations. The material may be a molded part and be selected to retain a desired shape and to be crush resistant so that the medical device product within the compartment is retained therein without being damaged. If viewing of the medical device product 512 within the product compartment 544 is desirable, then a transparent material may be used. Compatibility of a blister material with the product to be contained within the compartment may be an important factor in selection of a material for the shaped layer. In addition, the blister material is preferably formed of a material that ensures stability even when exposed to certain sterilization techniques (e.g., electronic beam sterilization or other light-based sterilization methods), such that it does not sustain damage or undergo an alteration that may result in structural weakening.

The shaped layer 540 is preferably formed with a contour that substantially corresponds to the shape of the medical device product 512. To ensure that the medical device product 512 is secured in a fixed position and fixed orientation within the protective package 520, the shaped layer 540 may include a region that is shaped and dimensioned to contact and grip or hold a region (e.g., a rigid portion not affected by contact) of the medical device product. In some embodiments, the shaped layer 540 is designed to grip only one region of the medical device product 512. However, in other embodiments, the shaped layer 540 is designed to contact and grip a plurality of regions of the medical device product 512 to provide additional securement of the medical device product. In these embodiments, the plurality of contact regions are discontinuous and not joined with each other. Generally, the contact region(s) of the shaped layer are designed to contact region(s) of the medical device product not sensitive to touch. For example, the contact region of the shaped layer may be designed to grasp regions of the sensor insertion device or the on-skin electronics housing unit, instead of the glucose sensor which is highly susceptible to damage from contact with other objects. As illustrated in FIG. 5B, in some embodiments, the shaped layer 540 comprises a shaped portions or latches 572, 574 that are designed to securely engage notches 372, 374 (see in FIGS. 3B-3E), such that such that movement of the protective package and/or the secondary container does not result in a shift in the position or orientation of the sensor insertion device relative to the protective package. It is contemplated that the shaped portions or latches may be of any of a variety of shapes and dimensions, as long as they serve to secure the product held in the protective package.

It has been found that the adhesive patch 382 (see FIG. 3B) which forms a part of the electronic housing unit is more susceptible to early peel-off from a wearer's skin (and thus a shorter usable lifetime) if the adhesive patch has been folded prior to use. To overcome this issue, in some embodiments, the shaped layer is formed with a contour that prevents contact between it and the adhesive patch. The contour may be shaped and dimensioned to discourage a user from removing the product by tugging or pulling on certain components that can be unintentionally detached prior to the proper time for detachment. For example, the safety lock 392, 592 of the product 512 can inadvertently become detached as the user tries to remove the product 512 from the protective package. To minimize this risk, in one embodiment, the contour of the shaped layer covering the safety lock 392, 592 is shaped to not allow for much space for a finger that a user would have to use to remove the product 512 from the protective package. This general design concept is also applicable to other components in which it is desirable to prevent inadvertent or unintentional detachment. To minimize the risk of the inadvertent detachment and to facilitate safe removal of the product, as illustrated in FIG. 5B, the shaped layer may designed with an portion 582 shaped and dimensioned to allow a user's finger to safely pull out and remove the product 512 at a portion of the product 512 that is not sensitive to touch and not likely to detach.

The backing layer 542 may be formed from a rupture and puncture resistant material, such as a tear-resistant lamination. The material of blister backing layer may be selected to be compatible with the material of the shaped layer, such as for heat sealability. Additionally, as with the shaped layer, compatibility of the shaped layer material with the medical device product to be contained within the compartment 544, barrier properties, such as, but not limited to, those that would contribute to stability of the product, may be important considerations in selecting the material of the backing layer 542. Moreover, in certain embodiments, the material may be designed to be impermeable to microorganisms, but permeable to moisture vapor and sterilant gas (e.g., ethylene oxide, hydrogen peroxide[1] and ozone), if a sterilant gas technique is employed in replacement of (or in addition to) a light-based sterilization technique. Exemplary materials that may be used for the backing layer include, without limitation, polyvinyl chloride, polyvinylidenechloride, polyacrylonitrile, polyethylene (e.g., a high-density polyethylene fiber, such as, DuPont™ Tyvek®), polyethylene terephthalate, polyethylene naphthalate, polypropylene, polyacrylate, cyclic olefins, polystyrene, polyesters, polyamides, ethylene vinyl alcohol, polyvinyl alcohol, and copolymers thereof; and paper. Similar to the shaped layer, the backing layer material is preferably formed of a material that permits exposure to certain sterilization techniques (e.g., electronic beam sterilization or other light-based sterilization methods or sterilant gas methods) without sustaining damage or undergoing an alteration that may result in damage to the medical device product.

In some embodiments, the protective package may be configured to be impermeable to water vapor and/or oxygen, so as to permit certain control of the atmospheric environment defined by the sealed compartment. A protective package of this type would be suitable for applications designed for medical devices that have a moisture-sensitive or oxygen-sensitive component, for example, a component made of a polymer which is subject to hydrolytic degradation and/or a component that undesirably undergoes a change in a certain property (e.g., sensitivity to glucose) when exposed to changes in moisture. For these applications, a material permeable to moisture and/or oxygen exchange (e.g., a high-density polyethylene fiber, such as, DuPont™ Tyvek®) would not be used. Instead, to avoid undesirable chemical reactions related to oxidation and hydrolysis reactions with the oxygen and/or moisture in air, materials that are impermeable to moisture vapor and/or oxygen would be used. These materials include, without limitation, certain polymers or plastic foil comprised of polyethylene, polypropylene, polyvinyl chloride, or any other types of plastic foils, or metal sheets such as aluminum foil, or any combinations thereof.

The backing layer 542 may be imprinted with information relating to the medical device product. The information may include a lot number corresponding to the manufacturing of the medical device product to account for potential lot-to-lot variations sensors to ensure accurate sensor results. In some embodiments, the backing layer 542 includes information that facilitates calibration of the sensor.

In some embodiments, the protective package 520 may be designed such that the backing layer contacts the medical device product at one or more regions. This contact may be in addition to any contact provided between the shaped layer and the medical device product. Like the shaped layer, the contact region(s) of the backing layer are designed to contact region(s) of the medical device product not sensitive to touch. FIG. 5C provides a perspective view of the protective package of FIG. 5A after it has been assembled and sealed.

Figure 6:
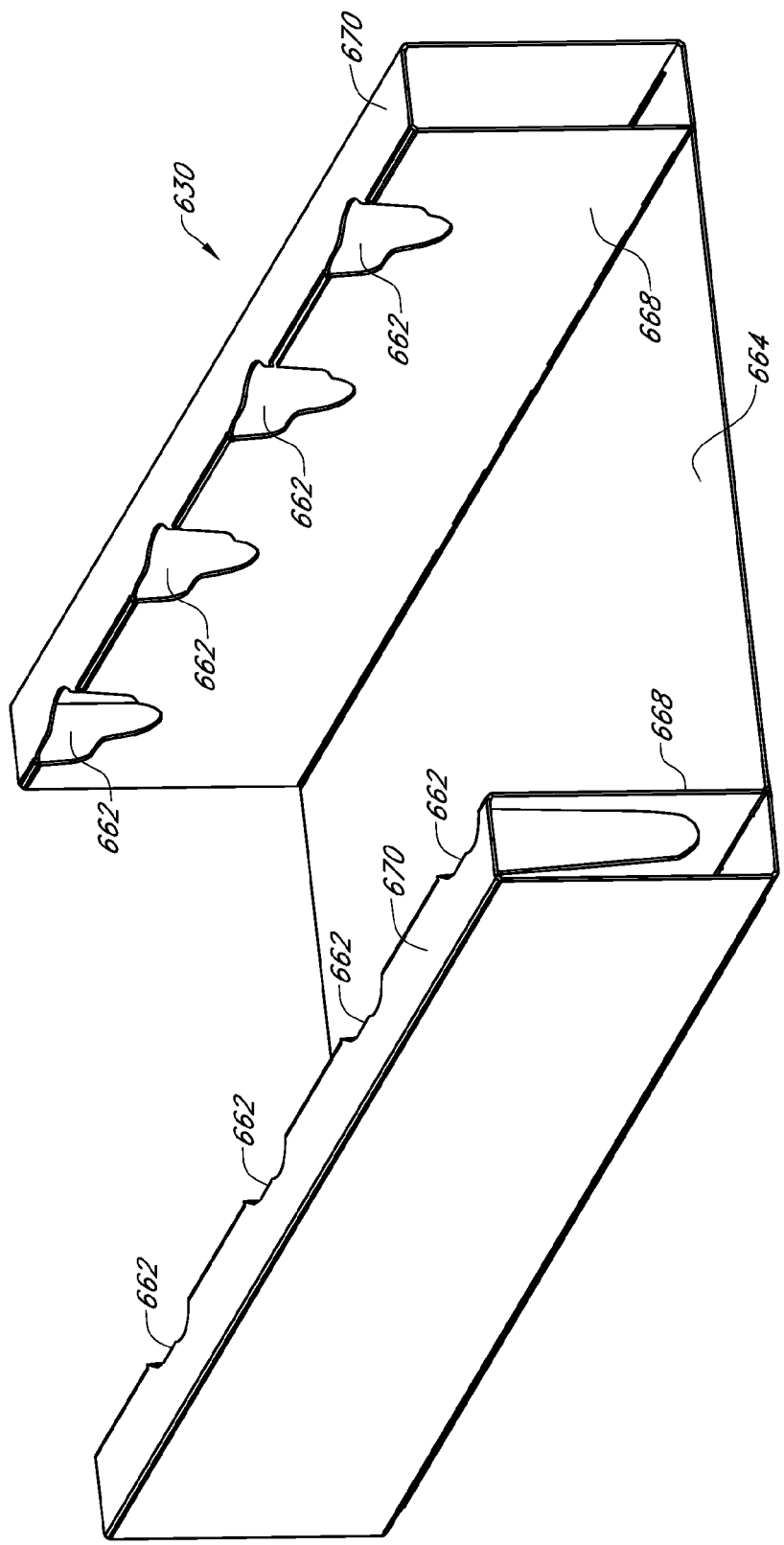
FIG. 6 is a perspective view of a retainer configured to secure protective packages (and the products received therein) in fixed positions within the second container.

Referring back to FIG. 4, the packaging system 400 also includes a secondary container 410 and a retainer 430 or tray shaped and dimensioned to secure one or more protective packages 420, 520 in a fixed position and fixed orientation within the secondary container 410. To provide this securement, the retainer 430 includes cut-outs shaped and dimensioned to conform to certain portions of the shaped layer. In the embodiment shown, the retainer 430 is a piece that is inserted into the secondary container 410. As illustrated in FIG. 6, which provides a close-view of the retainer 630, the retainer 630 includes a base 664 and a plurality of side walls 668 comprising the cut-outs 662. Each of the side walls 668 includes a ledge 670 that allows the protective package to be placed thereon. As illustrated, a pair of cut-outs 662 may be formed to accommodate different regions of a protective package's shaped layer. Accordingly, in this embodiment, each pair of cut-outs facilitates the securement of one protective package. The retainer 630 may include any number of cut-out pairs. In some embodiments, the retainer includes one pair of cut-outs to accommodate one protective package. However, in other embodiments, the retainer may include a two, three, four (as illustrated), five, six, nine, ten, twelve, sixteen, or more cut-out pairs to accommodate a corresponding number of protective packages. Along each of the side walls, the cut-outs are formed to be substantially evenly spaced apart from each other. Because of the substantially even spacing, each of the protective packages and the product contained therein are also substantially evenly spaced apart from each other. This arrangement permits each of the protective packages (and the medical device products contained therein) to receive substantially equal dosages of radiation during sterilization.

The base 664 and the plurality of side walls 668 are shaped and dimensioned to fit securely in the secondary container, such that movement of the secondary container 410 does not result in movement of the retainer 430, 630 therein. In turn, because of the securement provided by the retainer 430, 630 movement of the second container 410 does not result in movement of the protective package 420 and the medical device product disposed therein, relative to secondary container 410. In alternative embodiments, the retainer may be integral with the secondary container, such that the side walls of the secondary container are have cutouts formed thereto.

In some embodiments, the packaging system also includes a third container shaped and dimensioned to secure one or more second containers in a fixed position and fixed orientation within the third container 410. In certain embodiments, the third container is dimensioned and configured to hold only one level of a plurality of second containers. In other words, there are no second containers that are stacked on each other. By preventing stacking, the packaging system eliminates the risk of a shadow effect in which a container (holding a product) stacked on top of another container (also holding a product) blocks or reduces the amount of radiation from the E-beam apparatus from reaching the lower container, thereby resulting in unequal radiation dosage received by the products.

RFID (Radio Frequency Identification) technology may also be used to tag and trace products through the production and distribution chain. An RFID tag can be written or coded with specific manufacturing information, such as lot number, expiration date, final release status, etc., and then be used to communicate for tracking or data collection. Sometimes, RFID tags are used in packaging materials. RFID chips may rely on E²PROM (Electrically Erasable Programmable Read-Only Memory) for data storage. It has been found, however, that this type of memory is unable to maintain data integrity when exposed to irradiation at the levels typically required to sterilize medical devices using E-beam radiation in certain implementations. It has been unexpectedly found that FRAM (Ferroelectric Random Access Memory), a newly developed RFID technology, maintains data integrity even after exposure to a dose of 50 kGray radiation from an E-beam sterilization apparatus.

In some embodiments, one or more components of the sensor system and/or a portion of the packaging system incorporates an FRAM RFID chip. The FRAM RFID chip can be applied (e.g., adhered) to the outer surface of a glucose sensor system component(s) or packaging. Alternatively or additionally, the FRAM RFID chip can also be incorporated (e.g., molded) into the component or packaging. By incorporating the use of an FRAM RFID chip into the sensor system and/or the packaging system, the sensor system can then be sterilized through an E-beam (or other radiation-based) sterilization process performed at higher radiation level (e.g., at or greater than 50 kGray) than one that would typically damage conventional memory chips. It is contemplated that an FRAM RFID chip or any other memory chip capable of withstanding high radiation levels and maintaining data integrity after exposure to a dose of radiation (e.g., E-beam radiation) of 50 kGray for 30 seconds or more (e.g., 1 minute, 2 minutes, 3 minutes, 5 minutes, or 10 minutes) may be applied or incorporated into any portion of the packaging system and any component of the sensor system.

Method

Medical devices in many cases have to undergo sterilization prior to use by a patient. After sterilization, the protective package prevents the medical device product from containment. A sterile product is one which is free of viable microorganisms. The International Standards for sterilization of medical devices require, when it is necessary to supply a sterile product item, that adventitious microbiological contamination of a medical device from all sources be minimized by all practical means. Even so, product items produced under standard manufacturing conditions in accordance with the requirements for quality management systems for medical devices may, prior to sterilization, have microorganisms on them, albeit in low numbers. Such products are non-sterile. The purpose of sterilization processing is to inactivate the microbiological contaminants and thereby transform the non-sterile items into sterile ones.

Because of the package design disclosed herein, the medical device products held within the package are substantially prevented from shifting to different positions and/or orientations within the package prior to and during sterilization. Thus, during sterilization, the implantable analyte sensors each receive different amounts of radiation and a different radiation profile. This difference in radiation dosage may result in inconsistent sensor properties and thus inconsistent sensor performance among sensors. Accordingly, it is desirable to package the sensors in a manner that prevents or substantially inhibits sensor movement within the package. It is also desirable to sterilize the sensors in a manner that permits consistency in radiation dosage received and consistency in radiation profile.

Figure 7:
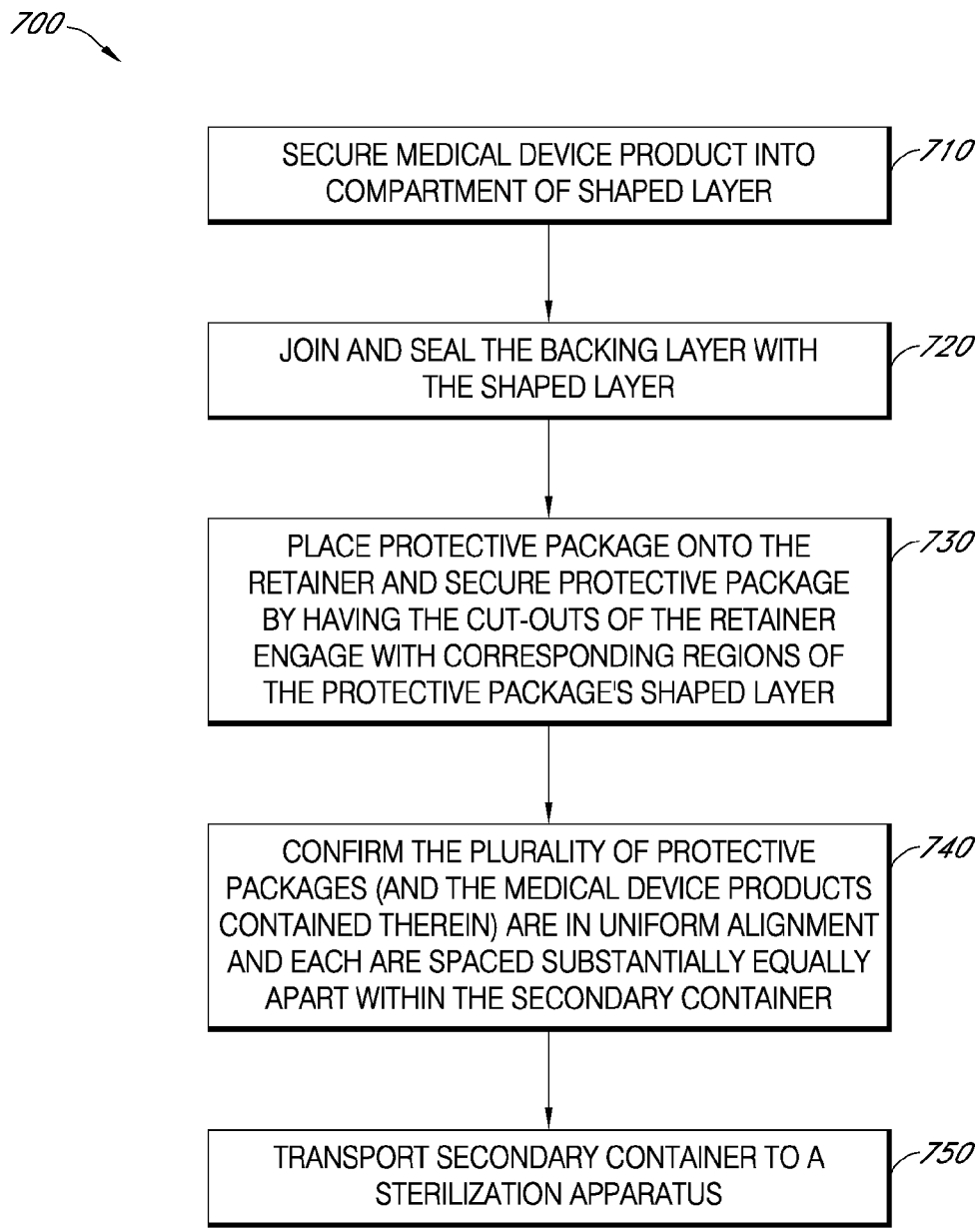
FIG. 7 is a flowchart illustrating an embodiment of a method for packaging and sterilizing a medical device.

With reference to FIG. 7, one embodiment of a method for sterilizing a medical device product comprises the following steps. In Box 710, an operator places and secures the medical device product (e.g., a continuous glucose sensor, an electronics housing unit, and/or an sensor insertion devices) into a compartment of the shaped layer in a manner such that a region of the shaped layer engages and grasps a corresponding region of the medical device product. Securement results in the medical device product being in a fixed position and fixed orientation within the protective package such that movement of the protective package does not result in shifting of the position or orientation of the medical device product therein. Next, in Box 720 the backing layer and the shaped layer are joined together by any sealing method known in the art that adequately seals the medical device product within the compartment. Exemplary sealing methods include heat sealing, adhesive seals (such as with heat-activated or solvent adhesive), RF or sonic seals, or any other suitable means. In some embodiments, the materials of the shaped layer and/or the backing layer may be pre-treated to facilitate sealing of such materials together. For instance, a coating may be applied to either or both materials to permit heat sealing. Through the above-described process, a protective package is formed, whereby the medical device product is secured therein and prevented from shifting its position or orientation relative to protective package. This process may be repeated to form a plurality of protective packages, each of which secures at least one medical device product.

In some embodiments, prior to sealing of the shaped layer to the backing layer, an inert gas is introduced to the compartment to control, reduce, and/or eliminate the oxygen content and/or moisture content in the compartment. Without being bound by theory, it is believed that the introduction of inert gas would substantially force all of the ambient air away from the entire surface area of the medical device product. Inert gases that may be used include, without limitation, nitrogen and noble gases (e.g., argon) may be used. In some embodiments, the inert gas is heavier than air, thereby allowing the inert gas injected to displace the ambient air surrounding the medical device product and purge the air away from the medical device product. In certain embodiments, to even further ensure that minimal or no ambient air remains in the compartment, prior to the introduction of the inert gas, the compartment undergoes vacuuming to remove ambient therefrom.

In Box 730, the protective package is placed onto the retainer and secured by making sure that the cut-outs of the retainer are engaged with corresponding regions of the shaped layer. This step may be repeated with packages designed to hold and secure a plurality of protective packages. In such situations, in accordance with Box 740, confirmation is made to ensure each of the plurality of protective packages (and the medical device products contained therein) are aligned in uniform orientation and each are spaced substantially equally apart within the secondary container. Thereafter, the lid of the secondary container is closed, and in Box 750, the second container is moved to a sterilization apparatus.

Sterilization may be performed by any of a variety of techniques. In some embodiments, sterilization is performed by light-based techniques (e.g., techniques utilizing gamma rays or x-rays). In further embodiments, an e-beam sterilization process is used in which the medical device product is transported via a conveyor system into a shielded booth where it is scanned. In certain embodiments, the packaging system that the sensors are contained in during sterilization is used for shipping the sensors to patients for use. In alternative embodiments, sterilization is performed by sterilant gas methods.

Figure 8:
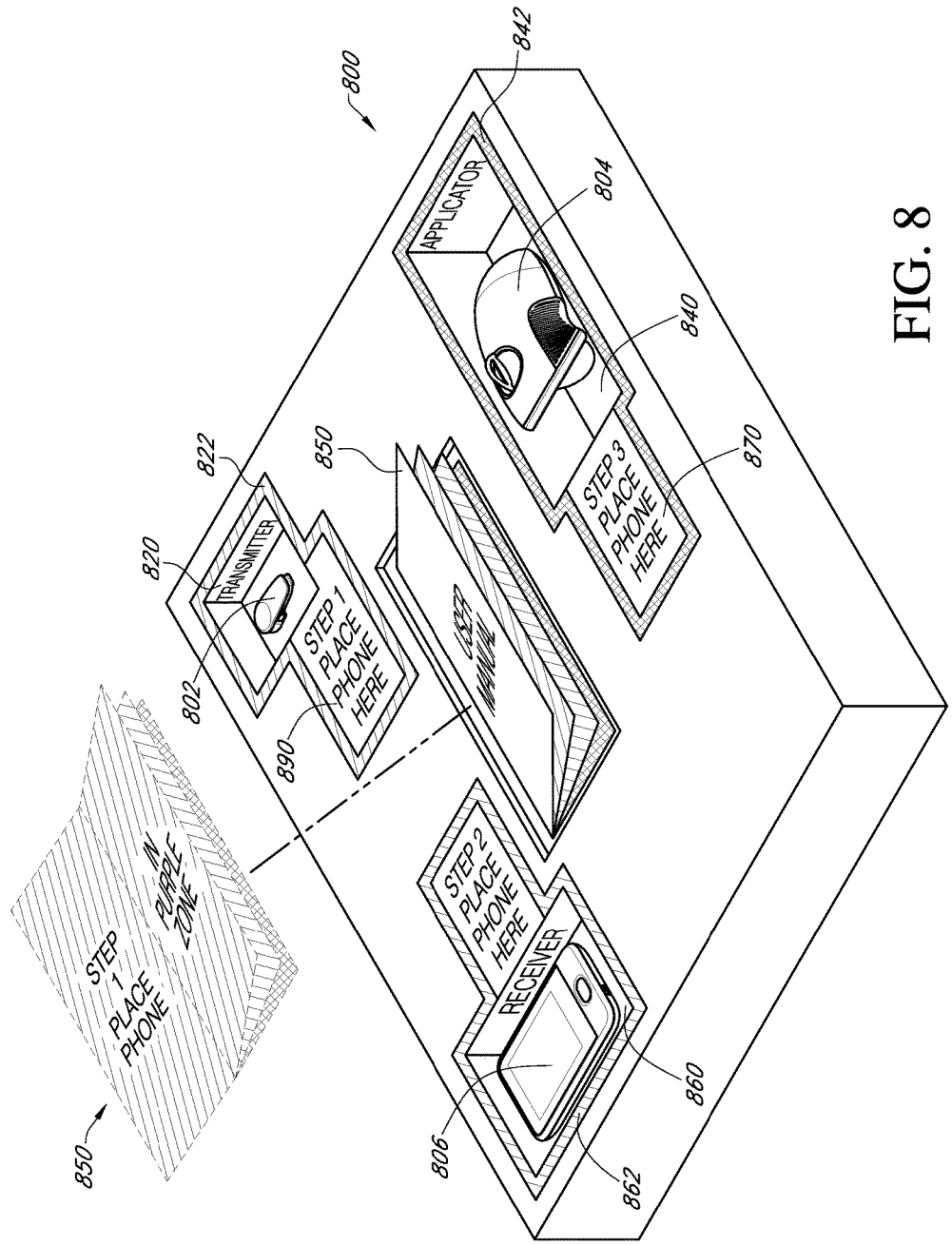
FIG. 8 is a perspective view illustrating one embodiment of an interactive packaging system.

In some embodiments, the packaging system is interactive and employs visual and/or audio features designed to help the user understand how to use the glucose sensor system. FIG. 8 illustrates one embodiment of a packaging system 800 with various components of the sensor system placed therein. As illustrated, components of the sensor system (e.g., the transmitter 802, the applicator 804, the receiver 806) are assigned to certain compartments 820, 840, 860 of the packaging system in which the compartments 820, 840, 860 are readily identifiable through certain visual characteristics (e.g., color coding 822, 842, 862 and/or number coding). During system setup, a video, pictures, and/or illustrations are shown to the user to provide a step-by-step tutorial on how to use glucose sensor system. The video, pictures, and/or illustrations may be provided with audio which describes the steps involved in the setup process. The videos, pictures, and/or illustrations may be played using any of a variety of electronic devices with a display, such as, for example, a receiver provided in the package, a smartphone, a computer, and/or a tablet.

The packaging (e.g., through use of a label on the packaging) or an article inside the packaging (e.g., a user manual 850) can be used to provide information for downloading an app (e.g., to a smartphone) or software (e.g. to a computer), so that the user can obtain and play the video on the receiver, smartphone, computer, or any other electronic devices capable of playing videos. The app or software may work in concert with the user manual 850 and/or packaging, which together are designed to provide the user with a cohesive, unified experience of unboxing and setting up the sensor system. For example, the cohesive, unified experience may include walking the user through a bluetooth pairing process (or any other step) using videos, pictures, or illustrations while the directions are audibly communicated to the user.

In certain embodiments, the packaging system employs near field communication (NFC) and/or other scanning technologies (e.g., technologies involving image or barcode scanning) to improve the experience of unboxing and setting up the sensor system. For example, the packaging system may include certain defined zones that can be identified by instructions, which can be number-coded and/or color-coded. For example, as illustrated in FIG. 8, the packaging system 800 has a zone 870 that has a barcode or image (not shown) for scanning and that is identified by an instruction (e.g., "Place Phone Here"). By following the instruction and thereby placing the phone in that particular zone, the phone is then enabled to read the code instantly using NFC or other scanning technologies, thereby eliminating the need for a user to manually enter a code. Instructions like these and the schemes used to make them readily identifiable to the user help avoid potential confusion.

In the embodiment illustrated in FIG. 8, the box employs color-coding and numbering that correspond to the various steps of the setup process. The same color-coding scheme may also be applied to the instruction manual. For example, the section of the user manual that correspond to Step 1 may have page edges (or entire pages) that have the same color as the zone 890 and compartment 820 corresponding to Step 1.

It has also been found that many users no longer desire tangible instruction guides, such as the traditional instruction guides in the form of a paper book. Indeed, tangible instruction guides may be more costly, yet less useful and less instructive than a digital version of an instruction guide, in particular if the digital version is interactive and easy for the user to navigate. In some implementations where a smart phone is used to download a glucose monitoring app and run the app, as described above, the initial download or launch of the app automatically triggers the phone to prompt the user as to whether the user would like to download a digital version of an instruction guide. If the user confirms that he or she would like to download the digital instruction guide, then the phone automatically requests a copy from a remote server with access to the instruction guide, which may be the same remote server that provides the app or a remote server associated with the manufacturer of the glucose monitoring system, for example. The instruction guide may then be accessed through the glucose monitoring application or through a third party application that is used to access and organize digital books, such as so-called digital libraries.

To illustrate the above, the following is one specific implementation of downloading and accessing a digital instruction guide. In this implementation, the user's phone is an iPhone available from Apple, Inc., and the user downloads a continuous glucose monitoring (CGM) app using the iPhone from Apple Inc.'s App Store. Once the CGM application is downloaded, the user launches the application by selecting an icon displayed on the display screen of the iPhone. Upon launch, the CGM application causes the iPhone to trigger a pop-up prompt asking the user if the user would like to download the instruction manual to the iPhone. The download can be to a digital library, for example, Apple's iBooks digital library application. If the user confirms downloading the instruction manual, then the instruction manual is downloaded from a remote server, such as a server operated by Apple, Inc. and associated with iBooks, for example. Once downloaded, the user can launch the iBooks application and access the user instruction guide.

Kits

Kits are provided for monitoring continuously monitoring an analyte. The kits include a packaged product that is a combination of implantable analyte sensors, an electronics housing unit, a sensor insertion device for inserting the implantable analyte sensor into a host, and/or instructions for using the medical device product. The packaged sensors are in placed in protective packages, which are secured to a container by a retainer, such that the packaged sensors are aligned in uniform orientation and secured to prevent shifts in position or orientation relative to the package.

The above description presents the best mode contemplated for carrying out the present invention, and of the manner and process of practicing it, in such full, clear, concise, and exact terms as to enable any person skilled in the art to which they pertain to practice this invention. This invention is, however, susceptible to modifications and alternate constructions from those discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

It should be understood that the methods described in this document are merely examples, and some steps may be omitted or replaced by other steps. Furthermore, although the steps of the method are described in a particular order, the various steps need not be performed sequentially or in the order described.

Terms and phrases used in this document, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps; the term 'example' is used to provide instances of the item in discussion, not an exhaustive or limiting list thereof; and adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the products 'a' and 'an' should be construed as referring to one or more than one (i.e., to at least one) of the grammatical objects of the product. By way of example, 'an element' means one element or more than one element.

What is claimed is:

1. A package for receiving and securing a product, the package comprising:
    at least one product, each product comprising:
        an on-skin assembly comprising an adhesive patch configured to adhere to a host's skin;
        a transcutaneous glucose sensor operably connected to the on-skin assembly, wherein the glucose sensor comprises an electrode surrounded by a membrane configured to be exposed to interstitial fluid;
    at least one first container configured to receive and secure the at least one product therein, wherein the at least first container is configured to be permeable to water vapor;
    a second container configured to receive the at least one first container; and
    a retainer configured to secure the at least one first container in a fixed position and fixed orientation within the second container such that movement of the second container does not result in substantial movement of the first container within the second container.

2. The package of claim 1, wherein the at least one first container comprises a plurality of first containers, wherein the retainer comprises a plurality of regions each configured to secure one of the plurality of first containers.

3. The package of claim 2, wherein the plurality of regions of the retainer are spaced apart at an equal distance such that the plurality of first containers are spaced apart at an equal distance.

4. The package of claim 2, wherein the at least one product comprises a plurality of products, wherein the plurality of products are aligned in a uniform orientation.

5. The package of claim 1, wherein the retainer is an integral component of the second container.

6. The package of claim 1, wherein the retainer is an insert releasably attached to the second container.

7. The package of claim 6, wherein the retainer comprises an aperture or pocket shaped to receive and conform to a region of the first container.

8. The package of claim 1, wherein the on-skin assembly further comprises a housing configured to receive an electronics unit.

9. The package of claim 8, wherein the at least one product further comprises an insertion device configured to insert the glucose sensor into a host.

10. The package of claim 1, wherein the at least one first container comprises a shaped layer and a backing layer adhered to the shaped layer.

11. The package of claim 10, wherein the backing layer comprises:
    a material selected from the group consisting of polyvinyl chloride, polyvinylidenechloride, polyacrylonitrile, polyethylene, polyethylene terephthalate, polyethylene naphthalate, polypropylene, polyacrylate, cyclic olefins, polystyrene, polyesters, polyamides, ethylene vinyl alcohol, polyvinyl alcohol, and copolymers thereof; and
    paper.

12. The package of claim 10, wherein the shaped layer is a molded part with a chamber for receiving the at least one product.

13. The package of claim 10, wherein the shaped layer is formed of a film.

14. The package of claim 13, wherein the film comprises a polymer selected from the group consisting of polyvinyl chloride, polyethylene, polyethylene terephthalate, polyethylene terephthalate glycol, polyvinylidene chloride, polypropylene, polyethylene, styrene, and copolymers thereof.

15. The package of claim 10, wherein the shaped layer comprises at least one region configured to secure the at least one product in a fixed position and fixed orientation within the at least one first container such that movement of the at least one first container or the second container does not result in substantial movement of the at least one product within the at least one first container.

16. The package of claim 15, wherein the at least one region of the shaped layer comprises a plurality of regions configured to secure the at least one product in a fixed position and fixed orientation within the at least one first container.

17. The package of claim 10, wherein the shaped layer is shaped and dimensioned to prevent bending of the adhesive patch.

18. The package of claim 1, further comprising a third container, wherein the third container is dimensioned and configured to receive a plurality of second containers and secure the plurality of second containers in a fixed position and fixed orientation.

19. The package of claim 1, further comprising a third container, wherein the third container is dimensioned and configured to hold only one level of a plurality of second containers.

20. The package of claim 1, wherein the glucose sensor is sterilized.

* * * * *

UNITED STATES PATENT AND TRADEMARK OFFICE
CERTIFICATE OF CORRECTION

PATENT NO. : 10,029,043 B2
APPLICATION NO. : 15/625840
DATED : July 24, 2018
INVENTOR(S) : Minda McDorman Grucela et al.

Page 1 of 1

It is certified that error appears in the above-identified patent and that said Letters Patent is hereby corrected as shown below:

In the Specification

In Column 3 at Line 48, Change "the" to --of the--.

In Column 6 at Line 17, Change "a an" to --an--.

In Column 9 at Line 54, Change "hemactocrit;" to --hematocrit;--.

In Column 9 at Line 65, Change "andrenostenedione;" to --androstenedione;--.

In Column 10 at Line 13, Change "diptheria/tetanus" to --diphtheria/tetanus--.

In Column 10 at Line 29, Change "sissomicin;" to --sisomicin;--.

In Column 10 at Line 33-34, Change "Giardia duodenalisa," to --Giardia duodenalis,--.

In Column 10 at Line 41, Change "Trepenoma pallidium," to --Treponema pallidum,--.

In Column 10 at Line 42, Change "stomatis" to --stomatitis--.

In Column 10 at Line 63, Change "(barbituates," to --(barbiturates,--.

Signed and Sealed this
Eighth Day of January, 2019

Andrei Iancu
*Director of the United States Patent and Trademark Office*